United States Patent
Crabb et al.

(10) Patent No.: US 10,098,620 B2
(45) Date of Patent: Oct. 16, 2018

(54) COMPACTIONLESS TISSUE PUNCTURE CLOSURE DEVICE AND METHODS

(75) Inventors: Rachael A. Crabb, Plymouth, MN (US); Thomas A. Savard, Arden Hills, MN (US); Irwin S. Wolosky, Parsippany, NJ (US)

(73) Assignee: TERUMO PUERTO RICO, L.L.C., Caguas, PR (US)

( * ) Notice: Subject to any disclaimer, the term of this patent is extended or adjusted under 35 U.S.C. 154(b) by 704 days.

(21) Appl. No.: 13/181,013

(22) Filed: Jul. 12, 2011

(65) Prior Publication Data

US 2012/0010634 A1    Jan. 12, 2012

Related U.S. Application Data

(60) Provisional application No. 61/363,597, filed on Jul. 12, 2010.

(51) Int. Cl.
*A61B 17/08* (2006.01)
*A61B 17/00* (2006.01)
*A61B 17/04* (2006.01)

(52) U.S. Cl.
CPC ............ *A61B 17/0057* (2013.01); *A61B 2017/00623* (2013.01); *A61B 2017/00654* (2013.01); *A61B 2017/00898* (2013.01); *A61B 2017/0417* (2013.01); *A61B 2017/0496* (2013.01)

(58) Field of Classification Search
CPC ...... A61B 17/0057; A61B 2017/00623; A61B 2017/0496; A61B 2017/00898; A61B 2017/00654; A61B 2017/0417; A61B 2017/00588; A61B 2017/00601

USPC .................. 606/213, 215, 232, 236
See application file for complete search history.

(56) References Cited

U.S. PATENT DOCUMENTS

| | | | | |
|---|---|---|---|---|
| 5,021,059 A | * | 6/1991 | Kensey et al. ................ | 606/213 |
| 5,531,759 A | * | 7/1996 | Kensey ............. | A61B 17/0057 604/15 |
| 5,728,114 A | * | 3/1998 | Evans ................ | A61B 17/0057 128/887 |
| 5,810,884 A | * | 9/1998 | Kim .............................. | 606/213 |
| 6,045,569 A | | 4/2000 | Kensey et al. | |
| 6,090,130 A | | 7/2000 | Nash et al. | |
| 6,860,895 B1 | * | 3/2005 | Akerfeldt et al. ............ | 606/215 |
| 7,621,937 B2 | * | 11/2009 | Pipenhagen et al. ......... | 606/232 |

(Continued)

FOREIGN PATENT DOCUMENTS

| JP | S54113288 U | 8/1979 |
|---|---|---|
| JP | H09512461 A | 12/1997 |

(Continued)

OTHER PUBLICATIONS

PCT International Search Report for International Application No. PCT/US2011/001219, dated Oct. 13, 2011, (5 pp.).

*Primary Examiner* — Richard Louis
(74) *Attorney, Agent, or Firm* — Buchanan Ingersoll & Rooney PC

(57) ABSTRACT

A tissue puncture closure device includes a carrier tube, a suture, an anchor, and a sealing pad. The sealing pad maintains a constant or substantially constant shape from when positioned in the carrier tube to when removed from the carrier tube and positioned adjacent to the tissue wall puncture in a post-deployment position. The suture may retain the anchor and sealing pad in contact with the tissue wall without altering a shape of the sealing pad.

23 Claims, 11 Drawing Sheets

(56) References Cited

U.S. PATENT DOCUMENTS

| | | | |
|---|---|---|---|
| 2005/0125031 A1* | 6/2005 | Pipenhagen | A61B 17/0057 606/213 |
| 2006/0058844 A1 | 3/2006 | White et al. | |
| 2006/0265006 A1 | 11/2006 | White et al. | |
| 2006/0265007 A1* | 11/2006 | White | A61B 17/0057 606/232 |
| 2007/0005081 A1* | 1/2007 | Findlay et al. | 606/148 |
| 2007/0032823 A1 | 2/2007 | Tegg | |
| 2007/0032824 A1 | 2/2007 | Terwey | |
| 2007/0198059 A1 | 8/2007 | Patel et al. | |
| 2008/0065121 A1* | 3/2008 | Kawaura | A61B 17/0057 606/146 |
| 2008/0243182 A1 | 10/2008 | Bates et al. | |
| 2009/0270911 A1* | 10/2009 | Shipp | 606/213 |

FOREIGN PATENT DOCUMENTS

| | | |
|---|---|---|
| JP | 2007512904 A | 5/2007 |
| JP | 2008061837 A | 3/2008 |
| WO | 9529635 A1 | 11/1995 |

* cited by examiner

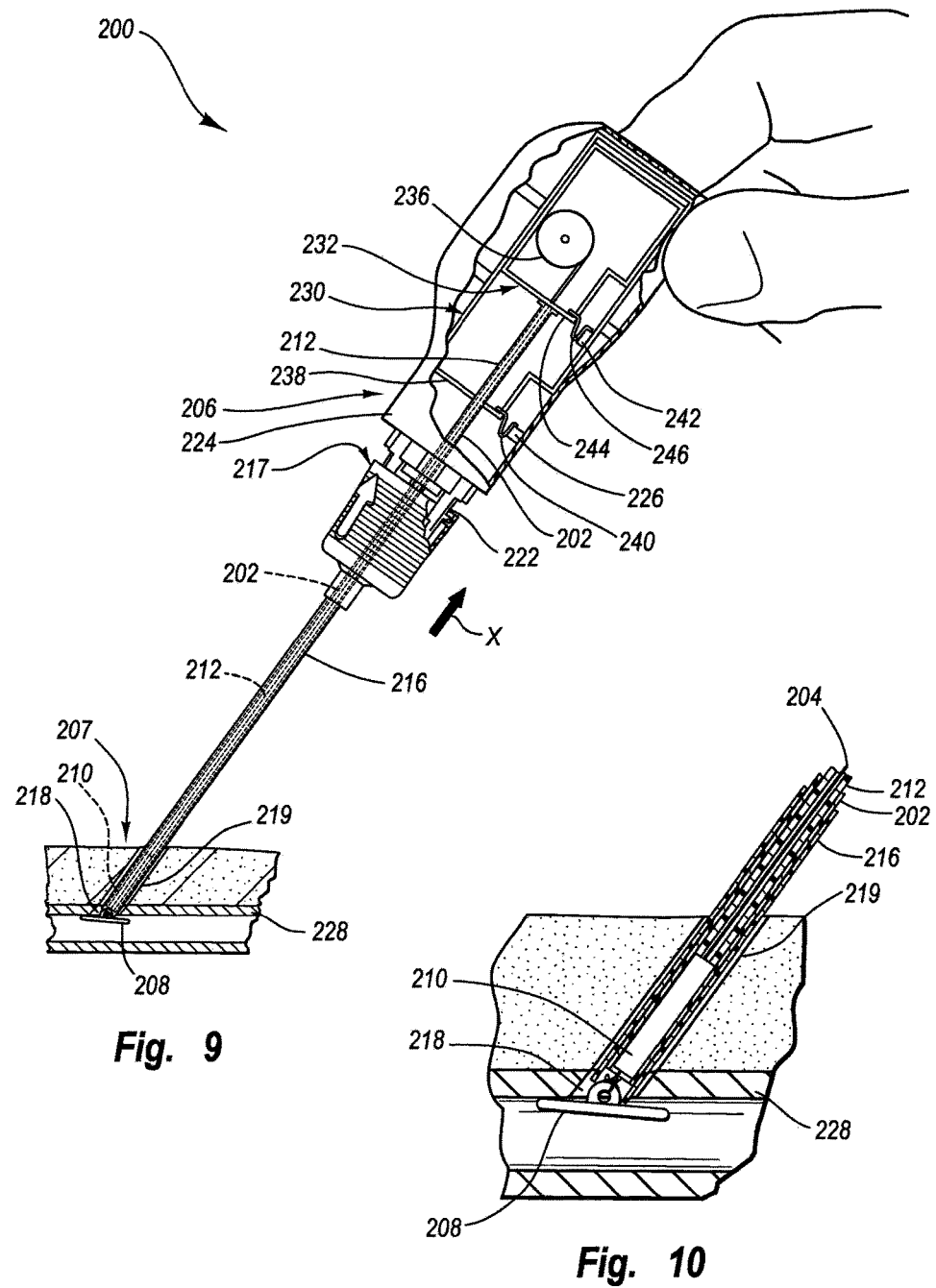

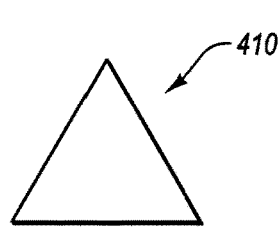
Fig. 21
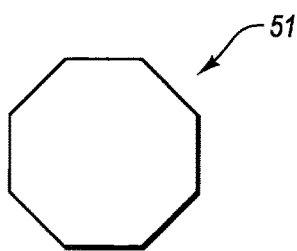
Fig. 22
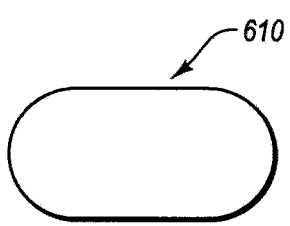
Fig. 23
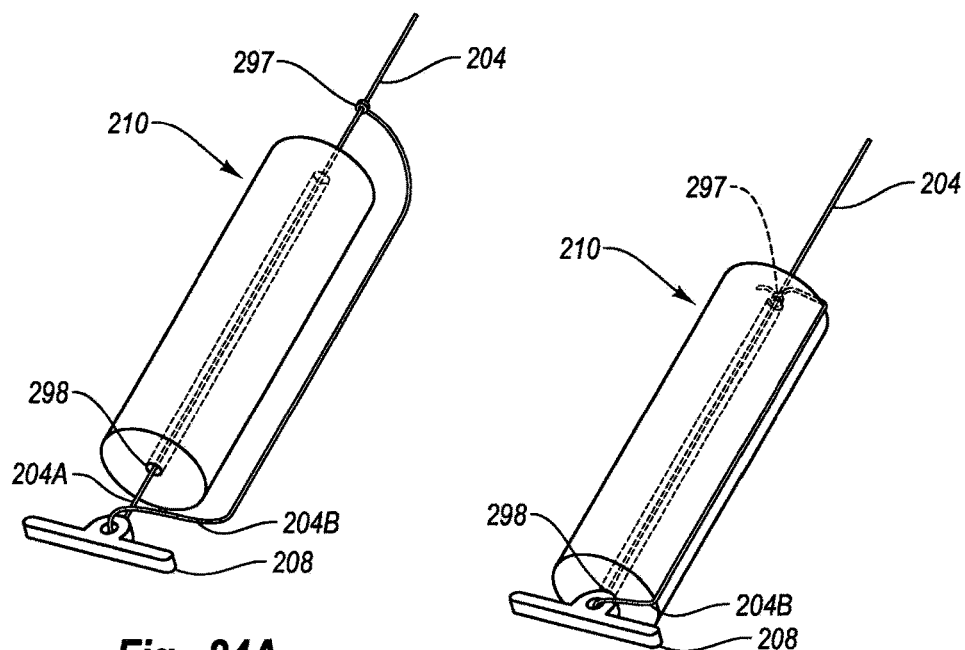
Fig. 24A
Fig. 24B

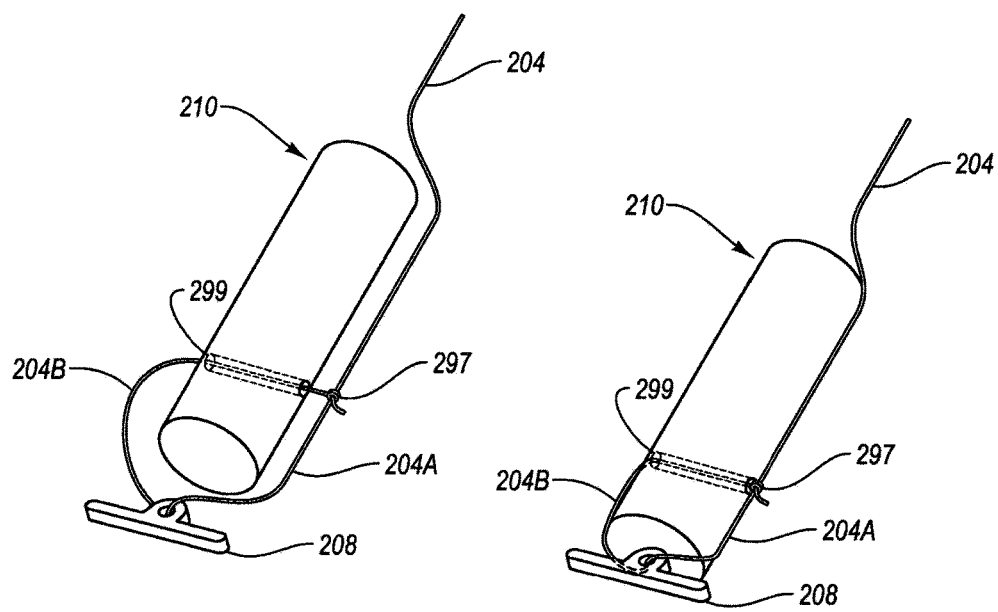
Fig. 25A
Fig. 25B
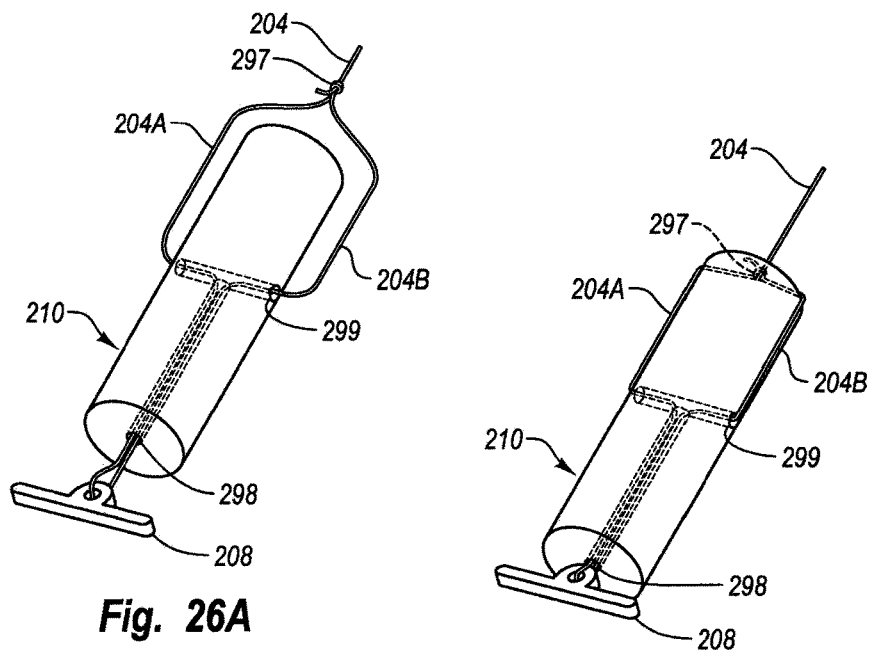
Fig. 26A
Fig. 26B

COMPACTIONLESS TISSUE PUNCTURE CLOSURE DEVICE AND METHODS

RELATED APPLICATION

This claims the benefit of U.S. Provisional Application No. 61/363,597, filed 12 Jul. 2010, which is hereby incorporated by reference herein in its entirety.

TECHNICAL FIELD

The present disclosure relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the vessel so that an insertion sheath can be placed in the vessel and thereafter instruments (e.g., catheters) can pass through the sheath and to an operative position within the vessel. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130 and 6,045,569, which are hereby incorporated in their entireties by this reference.

Typical closure devices such as the ones described in the above-mentioned patents place a sealing pad at the tissue puncture site. Deployment of the sealing pad may include manually ejecting the sealing pad from within a device sheath and compacting the sealing pad against an outer surface of the tissue puncture using a positioning member. The compacting procedure may begin after the device sheath (within which the positioning member may be located) has been removed. The construction of the sealing pad itself may require a predetermined amount of compaction force and a certain suture path through the sealing pad in order to avoid only a partial seal and associated late bleeding from the tissue puncture. Accordingly, there is a need for improving intravascular and intraluminal procedures and devices.

SUMMARY

One aspect of the present disclosure relates to a tissue puncture closure device for partial insertion into and sealing of a tissue wall puncture. The tissue puncture closure device includes a carrier tube, a suture, an anchor, and a sealing pad. The suture extends from a first end of the closure device to a second end of the closure device. The anchor is insertable through the tissue wall puncture and is attached to the suture at the second end of the closure device. The sealing pad is slidingly attached to the suture and carried in the carrier tube in a pre-deployment position. The sealing pad maintains a constant or substantially constant shape from when positioned in the carrier tube to when removed from the carrier tube and positioned adjacent to the tissue wall puncture in a post-deployment position.

The tissue puncture closure device may further include a housing positioned at the first end of the closure device, and at least one slide member positioned in and movable relative to the housing. The at least one slide member may include first and second slides, the second slide being positioned in and movable relative to the housing, and the first slide being carried by and movable relative to the second slide. The tissue puncture closure device may also include a suture spool having a portion of the suture wound thereon. The suture spool may be carried by the first slide. The tissue puncture closure device may include an insertion sheath through which the carrier tube is inserted, wherein the insertion sheath is connected to the housing, and the carrier tube is connected to the first slide. The tissue puncture closure device may include a positioning member positioned in the carrier tube and in contact with a proximal end of the sealing pad. The positioning member may be connected to the second slide, and the suture may extend through an interior of the positioning member. At least one automatic release member may be operable to release the first slide to move upon withdrawal of the closure device from the internal tissue wall puncture.

The sealing pad may include a generally circular cross-sectional shape. Alternatively, the sealing pad may include a non-circular cross-sectional shape. The sealing pad may be expandable in the post-deployment position upon absorption of a liquid. The sealing pad may be constructed as an integral, single piece member. The positioning member may maintain a position adjacent to the sealing pad while the carrier tube is withdrawn proximally relative to the sealing pad to provide the sealing pad in the post-deployment position, and the positioning member may be removed from contact with the sealing pad without changing a shape or size of the sealing pad.

Another aspect of the present disclosure relates to a tissue puncture closure device for partial insertion into and sealing of a tissue puncture in an internal tissue wall. The tissue puncture closure device may include an anchor, a sealing pad, and a suture. The anchor is configured for positioning on a distal side of the internal tissue wall. The sealing pad is configured for deployment from the tissue puncture closure device on a proximal side of the internal tissue wall. The suture is connected at a distal end to the anchor and sealing pad for slideably cinching the anchor and sealing pad together about the tissue puncture. The sealing pad may be slideably disposed on the suture proximal of the anchor. The sealing pad maintains a constant or substantially constant shape prior to and after being cinched to the anchor with the suture.

The tissue puncture closure device may also include a positioning member disposed on the suture and positioned proximal of the sealing pad. The positioning member may maintain the sealing pad in a fixed position relative to the tissue puncture prior to and after deployment of the sealing pad on the proximal side of the internal tissue wall. The tissue puncture closure device may include a housing arranged proximal of the anchor and sealing pad, a storage spool positioned in the housing onto which a proximal end of the suture is wound, and a carrier tube. The sealing pad may be positioned in the carrier tube prior to deployment, and a proximal end of the carrier tube may terminate in the housing. The tissue puncture closure device may include a first slide member positioned in and movable relative to the housing. The carrier tube may be connected to the first slide member and the first slide member carries the spool.

A further aspect of the present disclosure relates to a method of sealing a puncture in a vessel, wherein the puncture is accessible through a percutaneous incision. The method may include providing a tissue puncture closure device including a suture, an anchor, and a sealing pad, inserting the anchor through the tissue puncture and into the vessel, positioning the sealing pad within the percutaneous incision in a pre-deployment position, and deploying the sealing pad from the tissue puncture closure device adjacent to the puncture outside of the vessel. The sealing pad may maintain a constant or substantially constant shape from the pre-deployment position to a post-deployment position.

The method may also include providing an insertion sheath and a carrier tube, and the sealing pad is positioned in the carrier tube in the pre-deployment state. The method may include inserting the insertion sheath into the vessel puncture, wherein inserting the anchor includes inserting the anchor through the insertion sheath and into the vessel. The method may include cinching the sealing pad and anchor together with the suture, wherein the sealing pad maintains a constant shape prior to and after being cinched. The method may also include providing a positioning member in the carrier tube proximal of the sealing pad, wherein deploying the sealing pad in the percutaneous incision includes withdrawing the carrier tube and maintaining the sealing pad in a fixed position relative to the puncture with the positioning member without compacting the sealing pad.

Additional advantages and novel features of the invention will be set forth in the description which follows or may be learned by those skilled in the art through reading these materials or practicing the examples disclosed herein.

BRIEF DESCRIPTION OF THE DRAWINGS

The accompanying drawings illustrate various embodiments of the present invention and are a part of the specification. The illustrated embodiments are merely examples and do not limit the scope of the present disclosure.

FIG. 9 is a perspective view of an example tissue puncture closure device having compactionless sealing pad delivery capabilities according to the present disclosure, the tissue puncture closure device being inserted into a procedure sheath and shown engaged with a vessel in a first position.

FIG. 10 is a detailed inset of FIG. 9.

FIGS. 21-23 are end views of several additional example sealing pads according to the present disclosure for use with the tissue closure device of FIG. 9.

FIGS. 24A, 25A and 26A are perspective views of several example suture threading configurations according to the present disclosure for use with the tissue closure device of FIG. 9, wherein the sutures are loose fit about the sealing pad.

FIGS. 24B, 25B and 26B are perspective views of the suture threading configurations of FIGS. 24A, 25A and 26A, respectively, with the suture having a close fit about the sealing pad.

Throughout the drawings, identical reference numbers designate similar, but not necessarily identical, elements.

DETAILED DESCRIPTION

Figure 1:
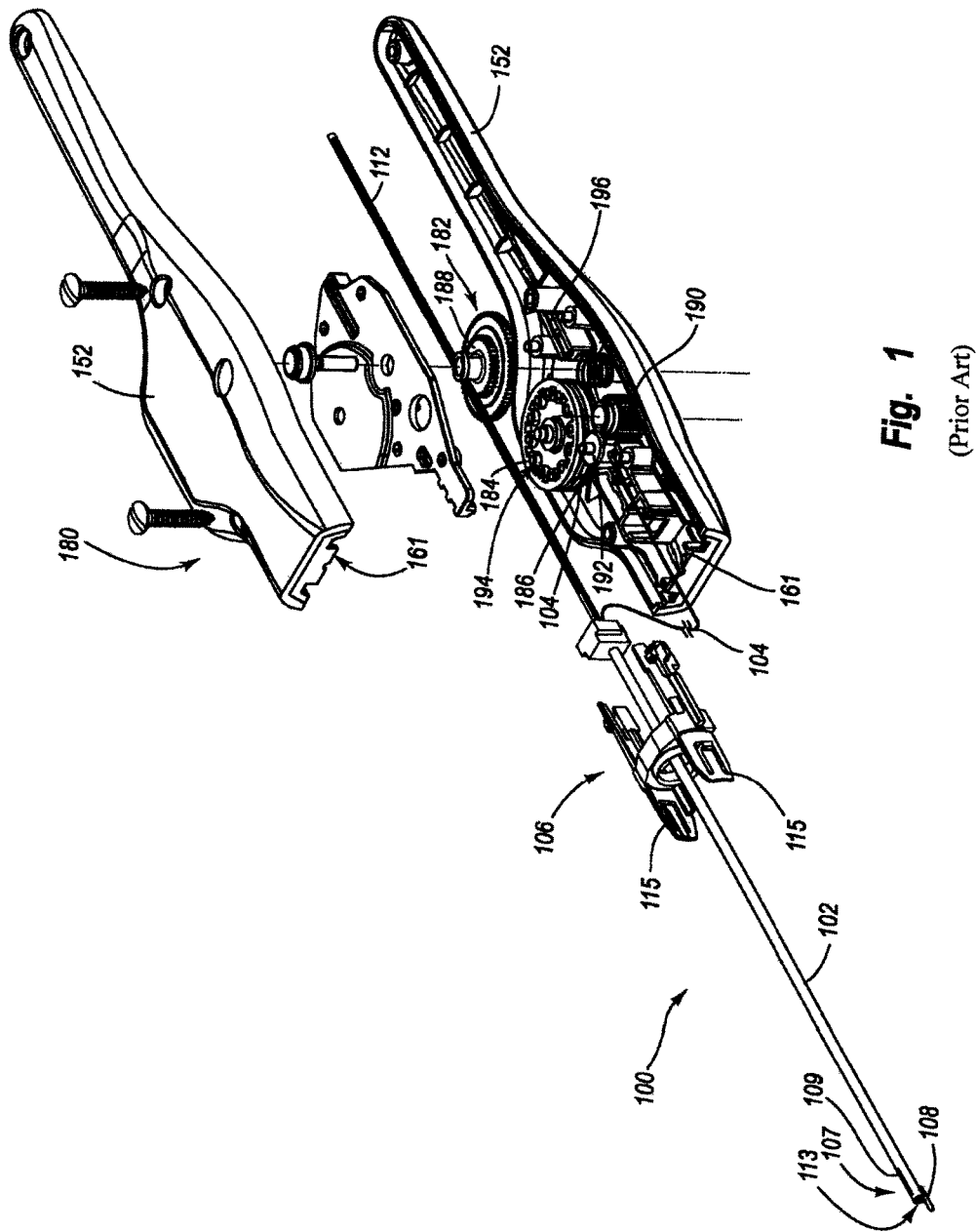
FIG. 1 is a perspective assembly view of a tissue puncture closure device with an automatic compacting or driving mechanism according to the prior art.

As mentioned above, vascular procedures are conducted throughout the world and require access to a vessel through a puncture. In some cases, the vessel is a femoral artery. To close the puncture following completion of the procedure, many times a closure device is used to sandwich the puncture between an anchor and a sealing pad. However, sometimes the sealing pad is difficult to eject from the sealing device and may not properly seat against an exterior situs of the arteriotomy. If the pad does not seat properly against the arteriotomy, there is a potential for prolonged bleeding. The present disclosure describes methods and apparatus that facilitate sealing pad ejection and proper placement of the sealing pad. While the vascular instruments shown and described below include procedure sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims.

The present disclosure is directed to a tissue puncture closure device (generally referred to as a "closure device") that includes a sealing pad, an anchor, a suture, a carrier tube, and a positioning member. The closure device is configured to deposit the anchor on a distal side of the puncture, position the sealing pad adjacent to a proximal side of the tissue puncture, and secure the sealing pad to the anchor with the suture. The closure device is configured to seal the puncture with the sealing pad without compacting the sealing pad. This type of closure device may be referred to as a "compactionless" closure device, or a compactionless intraluminal or intravascular closure device. The closure device is considered intraluminal or intravascular because it includes a component (i.e., the anchor) that is deposited in the vessel (i.e., on a side of any tissue puncture opposite the sealing pad). Such factors as the construction of the sealing pad, the suture path through the sealing pad, and the location of the knot tied in the suture that provides a positive connection between the sealing pad and anchor may all lend to the ability of the closure device to provide sealing of the puncture without compacting the sealing pad.

The closure device may also include a housing and multiple slide members positioned in the housing. The slide members may account for retraction or withdrawal of the insertion sheath and carrier tube while maintaining the sealing pad in a fixed position adjacent to the puncture. In one arrangement, the closure device includes first and second slide members that are movable relative to each other and to the housing. The insertion sheath may be connected directly to the housing. The carrier tube may be connected to the first slide member. The positioning member, which maintains contact with a proximal end surface of the sealing pad, may be connected directly to the second slide member. The first and second slide members may automatically release in sequence relative to the housing at different times while withdrawing the closure device relative to the tissue puncture.

In one example, the sequence of releasing the first and second slides provide withdrawal of the insertion sheath from a percutaneous incision, followed by withdrawal of the carrier tube to expose the sealing pad in the percutaneous incision adjacent to the puncture. Withdrawing the closure device may automatically apply tension to the suture which results in a knot in the suture being advanced distally against the sealing pad to secure the sealing pad and anchor together. An extra length of the suture that is maintaining in the housing may be manually released to permit withdrawal of the positioning member from the percutaneous incision. The suture may be automatically or manually cut to release the closure device from the anchor and sealing pad.

As used in this specification and the appended claims, the term "compact" or "compacting" is used broadly to mean any type of tamping (i.e., packing down by one or a succession of blows or taps or smooth, steady pressure, but not by excessive force), compacting, or compressing. "Engage" and "engageable" are also used broadly to mean interlock, mesh, or contact between two devices. Likewise "disengage" or "disengagable" means to remove or capable of being removed from interlock, mesh, or contact. A "spool" is a cylinder or other device on which something else is at least partially wound. A "tube" is an elongated device with a passageway. A "lumen" refers to any open space or cavity in a bodily organ, especially in a blood vessel. "Slidingly mounted" means movable relative to an appropriate support. A "detent" is a catch or lever that locks, at least temporarily, the movement of one part of a mechanism. The words "including" and "having," as used in the specification, including the claims, have the same meaning as the word "comprising."

Referring now to the drawings, and in particular to FIGS. 1-8, a vascular puncture closure device 100 is shown according to the prior art. The closure device 100 is shown in an exploded perspective view in FIG. 1. FIGS. 2-7 illustrate the closure device 100 assembled and inserted through a procedure sheath 116 and into a lumen 132. The closure device 100 has particular utility when used in connection with intravascular procedures, such as angiographic dye injection, cardiac catheterization, balloon angioplasty and other types of recanalizing of atherosclerotic arteries, etc. as the closure device 100 is designed to cause immediate hemostasis of the blood vessel (e.g., arterial) puncture.

The closure device 100 includes a first or proximal end portion 106 and a second or distal end portion 107. A carrier tube 102 extends from the proximal end portion 106 to the distal end portion 107 and includes an outlet 113 at the distal end portion 107. The distal end portion 107 may include a slit 109 (see FIG. 1).

Figures 2, 3:
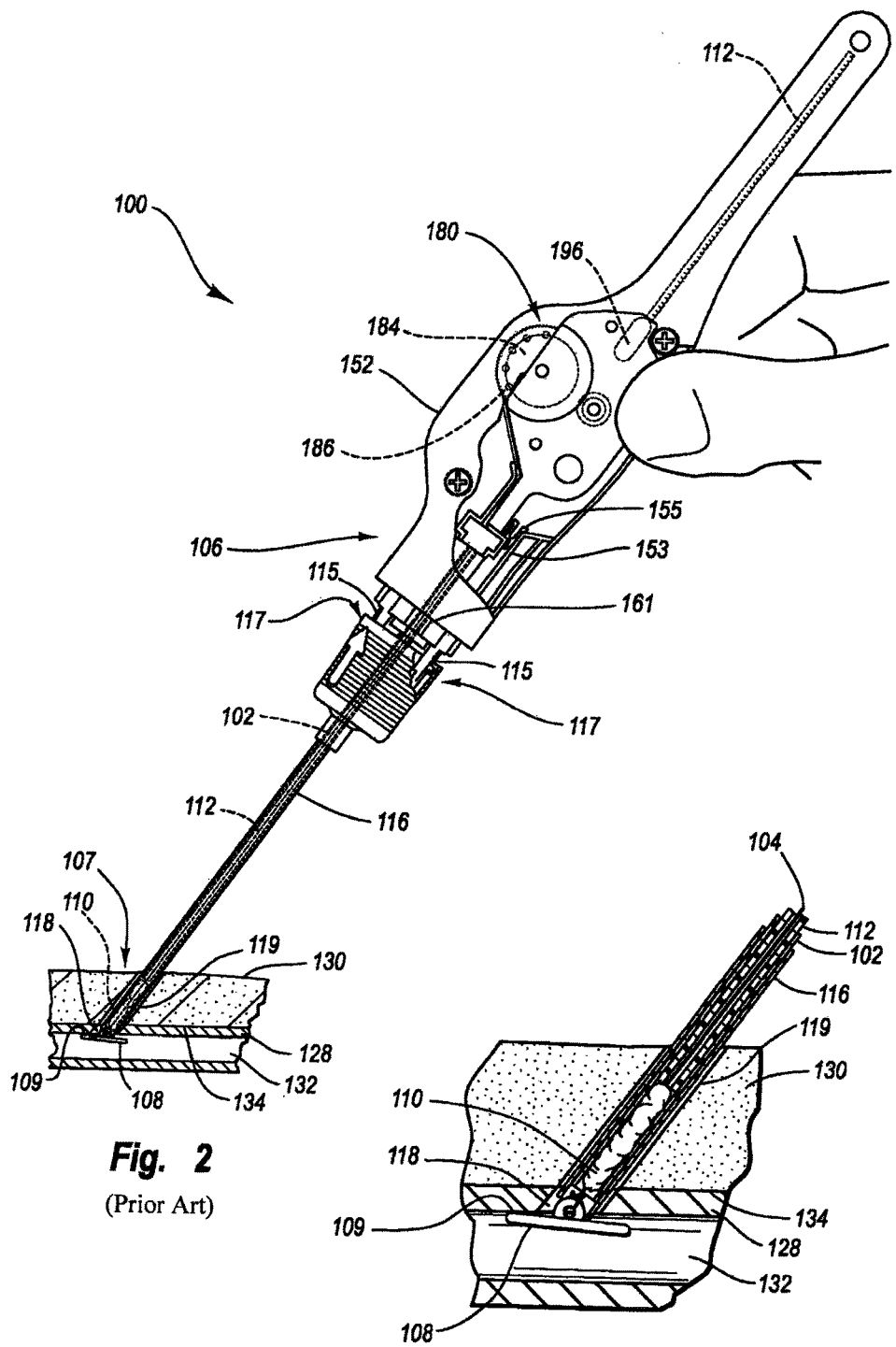
FIG. 2 is a side view of the tissue puncture closure device of FIG. 1 inserted into a procedure sheath and shown engaged with a vessel in a first position.
FIG. 3 is a detailed inset of FIG. 2.

The carrier tube 102 may be made of plastic or other material and is designed for insertion through the procedure sheath 116 (see FIG. 2). The procedure sheath 116 is designed for insertion through a percutaneous incision 219 in a tissue layer 130 and into the lumen 132. According to FIGS. 2-7, the lumen 132 may comprise an interior portion of a vessel 128 such as a femoral artery.

Figure 8:
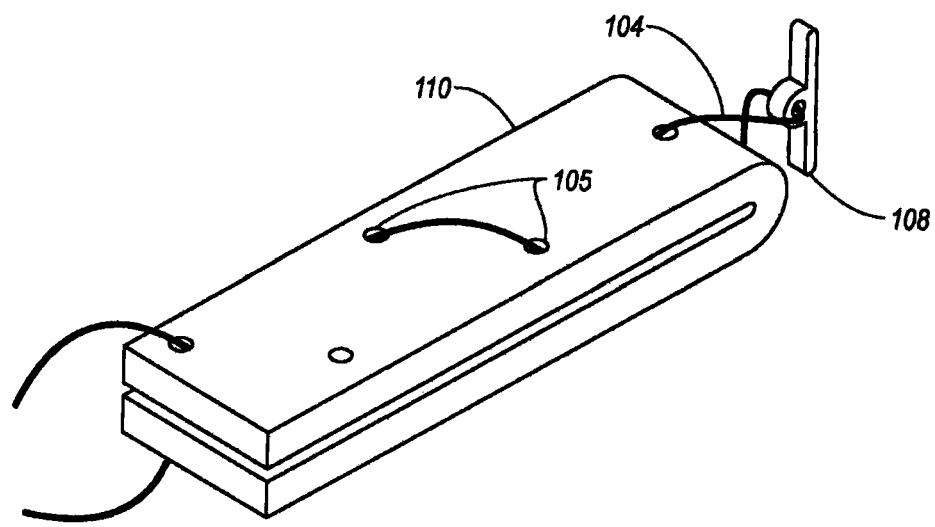
FIG. 8 is a perspective view of an example sealing pad, anchor and suture assembly for use with the tissue puncture closure device of FIG. 1.

At the distal end portion 107 of the carrier tube 102 there is an anchor 108 and a sealing plug 110. The anchor 108 is an elongated, stiff, low-profile member arranged to be seated inside the vessel 128 against a vessel wall 134 contiguous with a puncture 118. The anchor 108 is preferably made of a biologically resorbable polymer. The sealing plug 110 may be formed of a compressible sponge, foam, or fibrous mat made of a biologically resorbable material such as collagen. The sealing plug 110 is typically constructed as an elongate folded member having a rectangular cross-section as shown in FIG. 8.

The sealing plug 110 and anchor 108 are connected to one another by a suture or suture 104 that is also biologically resorbable. The anchor 108, the sealing plug 110, and the suture 104 are collectively referred to as the "closure elements" below. As shown in FIG. 1, the anchor 108 is initially arranged adjacent to and exterior of the distal end portion 107 of the carrier tube 102, while the sealing plug 110 is initially disposed within the carrier tube 102. The anchor 108 is shown nested in its low profile configuration along the carrier tube 102 to facilitate insertion into the lumen 132 in FIG. 1, and deployed with a surface abutting the vessel wall 134 in FIGS. 2-7.

The suture 104 extends distally from the proximal end portion 106 of the closure device 100 through the carrier tube 102. The suture 104 may be threaded through one or more perforations 105 in the sealing plug 110, through a hole in the anchor 108, and proximally back toward the carrier tube 102 to the sealing plug 110 (FIG. 8). The suture 104 is preferably threaded again through a perforation or series of perforations in the sealing plug 110. The suture 104 may also be threaded around itself to form a self-tightening slip-knot. The suture 104 may thus connect the anchor 108 and the sealing plug 110 in a pulley-like arrangement to cinch the anchor 108 and the sealing plug 110 together when the carrier tube 102 is pulled away from the anchor 108 and the sealing plug 110. The anchor 108 and the sealing plug 110 sandwich and lock together to seal the tissue puncture 118.

The threaded arrangement of the suture 104 in the sealing plug 110 may result in some torquing and rotation of portions of the sealing plug 110 when compacting the sealing plug 110 and cinching the anchor 108 and sealing plug 110 together. This torquing or rotation of the sealing pad 110 at locations along the length of the sealing pad 110 may change a cross-sectional shape of the sealing plug 110 from the rectangular shape shown in FIG. 8 to a more contoured shape such as a generally circular shape.

The carrier tube 102 houses a compacting device, such as a compacting tube 112 (see FIG. 1), for advancing the sealing plug 110 along the suture 104 and toward the anchor 108. The compacting tube 112 is shown located partially within the carrier tube 102 and proximal of the sealing plug 110. The compacting tube 112, however, also extends through a handle 152 of the closure device 100. The compacting tube 112 is an elongated rack that may be rigid or flexible. The suture 104 extends through at least a portion of the compacting tube 112. The suture 104 is not directly connected to the compacting tube 112. Accordingly, the suture 104 and the compacting tube 112 may slide past one another.

According to the embodiment of FIGS. 1-8, the suture 104 attaches to an automatic compacting assembly. The automatic compacting assembly may include an automatic driving mechanism 180, and the compacting tube 112. The automatic driving mechanism 180 is located within the housing or handle 152 at the proximal end portion 106 of the closure device 100.

In practice, the carrier tube 102 of the closure device 100 (containing the closure elements described above) is inserted into the procedure sheath 116, which is already inserted within the vessel 128 (see FIGS. 2-3). As the closure device 100 and the associated closure elements are inserted into the procedure sheath 116, the anchor 108 passes through and out of the distal end of the procedure sheath 116 and is inserted into the vessel lumen 132. As mentioned above and shown in FIG. 1, the anchor 108 is initially arranged substantially flush with the carrier tube 102 to facilitate insertion of the anchor 108 through the percutaneous incision 219 and into the lumen 132.

After the anchor 108 passes out of the distal end of the procedure sheath 116, however, it tends to deploy or rotate to the position shown in FIGS. 2-3. The closure device 100 may also be partially withdrawn from the procedure sheath 116, catching the anchor 108 on the distal end of the procedure sheath 116 and rotating it to the position shown in FIGS. 2-3. However, the closure device 100 preferably includes a pair of biased fingers 115 that are lockingly received by a matching pair of recesses 117 in the procedure sheath 116. The locking arrangement between the biased fingers 115 and matching recesses 117 preferably fixes the position of the handle 152 relative to the procedure sheath 116.

Following deployment of the anchor 108, the handle 152 and the procedure sheath 116 are withdrawn together. Withdrawing the handle 152 causes the anchor 108 to anchor itself within the vessel 128 against the vessel wall 134. With the anchor 108 anchored within the vessel 128 at the puncture 118, further retraction of the handle 152 and procedure sheath 116 tends to pull the sealing plug 110 out from the distal end portion 107 of the carrier tube 102, thereby depositing the sealing plug 110 within the incision or puncture tract 119. The slit 109 (see FIG. 1) in the carrier tube 102 allows the distal end portion 107 of the carrier tube to flex or open, facilitating ejection of the sealing plug 110. The slit 109 at the distal end portion 107 of the carrier tube 102 may be prevented from opening or flexing by the procedure sheath 116, which is concentric with the carrier tube 102. Therefore, retraction of the handle 152 and procedure sheath 116 causes the procedure sheath 116 to retract with respect to the carrier tube 102 to a second position shown in FIGS. 4-5.

Figures 4, 5:
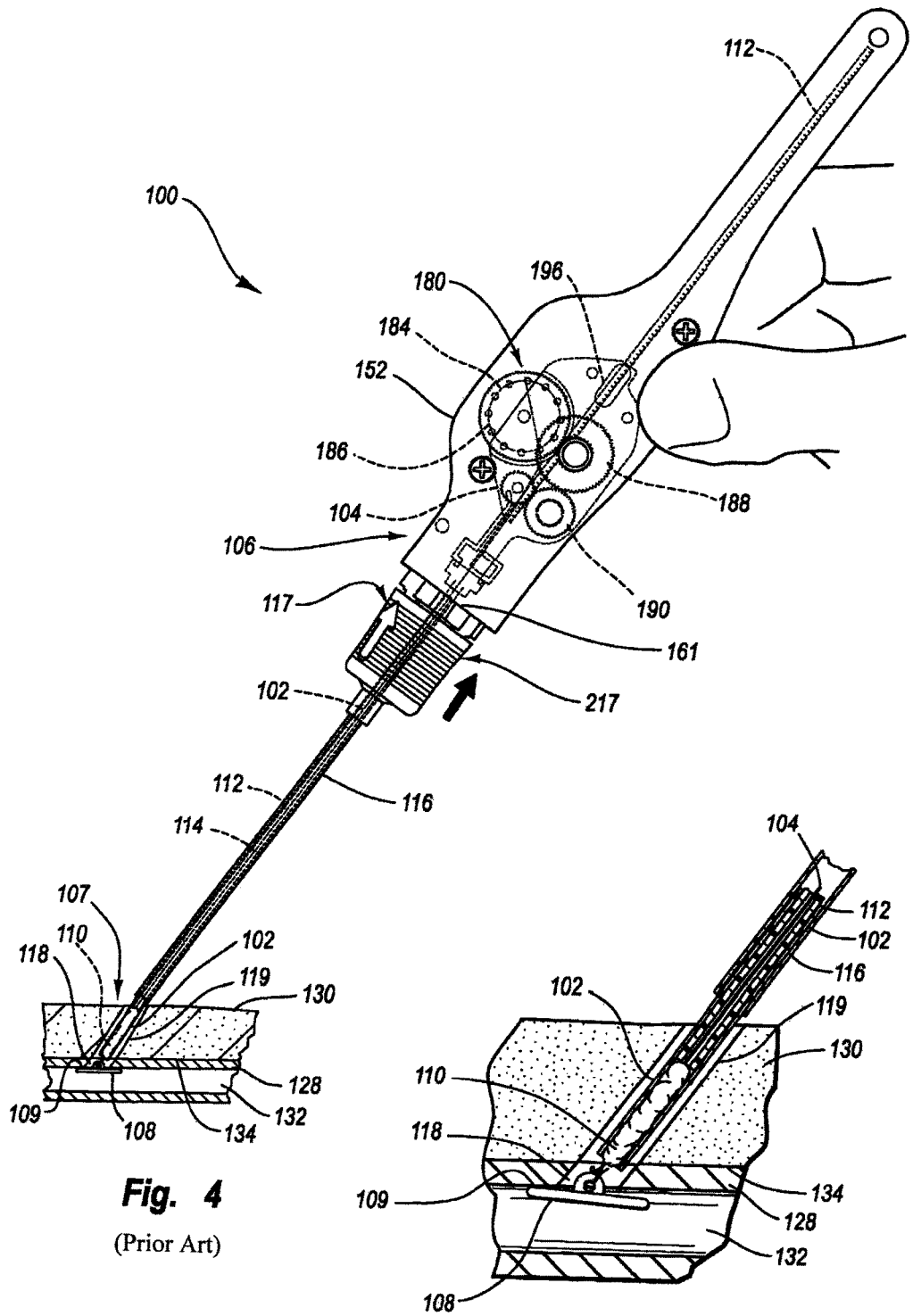
FIG. 4 is a side view of the tissue puncture closure device of FIG. 1 shown engaged with a vessel in a second position retracting the procedure sheath.
FIG. 5 is a detailed inset of FIG. 4.

Referring to FIGS. 4-5, the distal end portion 107 of the carrier tube 102 is exposed (within the puncture tract 119) as the handle 152 and the procedure sheath 116 are retracted. The carrier tube 102 retains its position relative to the puncture 118 until the handle 152 and the procedure sheath 116 have been retracted a predetermined distance. Relative movement between the handle 152 and the carrier tube 102 is facilitated by a sliding mount arrangement between the automatic driving mechanism 180 and the handle 152.

As shown by the combination of FIGS. 2-7, the automatic driving mechanism 180 (which is attached to the carrier tube 102) is preferably free floating or displaceable and slides relative to the handle 152 as the handle 152 and the procedure sheath 116 are retracted. However, the automatic driving mechanism 180 may be initially held in a first position relative to the handle 152 as shown in FIG. 2. For example, as shown in FIG. 2, the automatic driving mechanism 180 may comprise a temporary holder such as a stowage detent 155 slidingly mounted in a track 153 disposed in the handle 152. The stowage detent 155 temporarily holds the automatic driving mechanism 180 in the first position shown in FIG. 2 and limits premature sliding within the handle 152.

The stowage detent 155 releases when a sufficient predetermined force is applied between the handle 152 and the automatic driving mechanism 180. For example, with the anchor 108 deployed, a retraction force provided by a user to the handle 152 causes sliding movement between the automatic driving mechanism 180 and the handle 152. Accordingly, retraction of the handle 152 retracts the procedure sheath 116 (which is fixedly connected to the handle 152), but the automatic driving mechanism 180 and the carrier tube 102 slide relative to the handle 152 and therefore remain in position with respect to the puncture 118. The automatic driving mechanism 180 may slide a predetermined distance with respect to the handle 152. The predetermined distance is preferably at least long enough to fully expose the slit 109 (see FIG. 1) in the carrier tube 102.

Figures 6, 7:
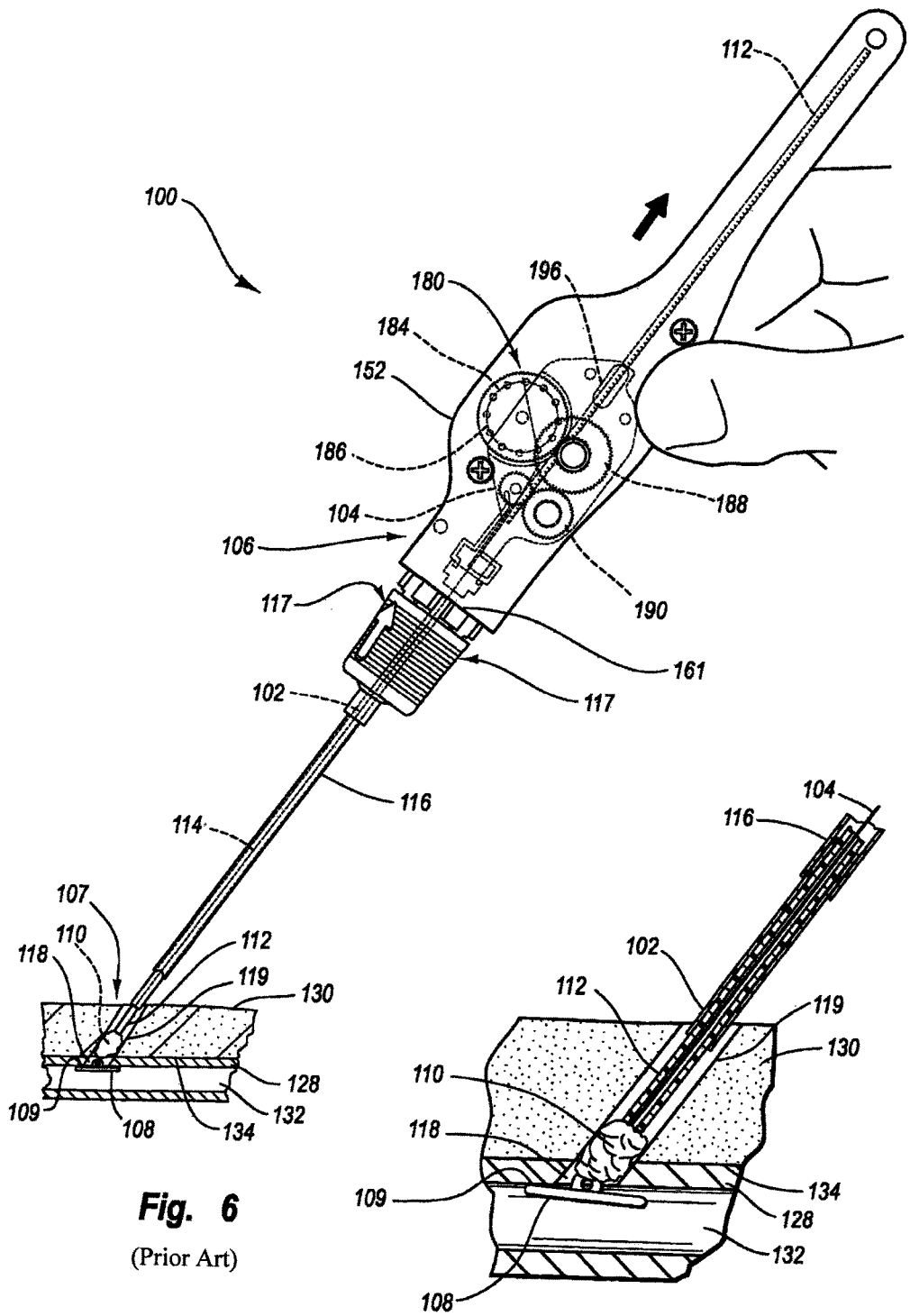
FIG. 6 is a side view of the tissue puncture closure device of FIG. 1 shown engaged with a vessel in a third position compacting a sealing plug.
FIG. 7 is a detailed inset of FIG. 6.

When the automatic driving mechanism 180 has slid the predetermined distance (see FIG. 4), further retraction of the handle 152 withdraws the carrier tube 102 as well, ejecting and compacting the sealing plug 110 automatically as shown in FIGS. 6-7. The closure device 100 may then automatically compact the sealing plug 110. The sealing plug 110 is compacted while the carrier tube 102 is being withdrawn, reducing or eliminating any gaps that may otherwise occur between the sealing plug 110 and the puncture 118 in the vessel 128.

In addition, by placing tension on or pulling the suture 104 away from the puncture tract 119, the suture 104 may cinch and lock (with a slip knot or the like) together the anchor 108 and the sealing plug 110, sandwiching the vessel wall 134 between the anchor 108 and sealing plug 110. The force exerted by the compacting tube 112 and the cinching together of the anchor 108 and sealing plug 110 by the suture 104 also causes the sealing plug 110 to deform radially outward within the puncture tract 119 and function as an anchor on the proximal side of the tissue puncture 118 as shown in FIGS. 6-7.

The compacting tube 112 is automatically driven toward the sealing plug 110 by the automatic driving mechanism 180. One embodiment of the automatic driving mechanism 180 is shown in detail in FIG. 1. The automatic driving mechanism 180 may comprise a gearbox assembly 182, and the gearbox assembly 182 may be selectably disengagable. According to the embodiment of FIG. 1, once the automatic driving mechanism 180 contacts the stop 161, further retraction of the closure device 100 automatically effects compacting of the sealing plug 110 (see FIG. 6).

According to the gearbox assembly 182 of FIGS. 1 and 6, the suture 104 is connected to and partially wound about a spool 184 of a first gear and spool assembly 194 (see FIG. 1). The first gear and spool assembly 194 includes both the spool 184 and a first gear 186. The first gear 186 is connected to the spool 184 and therefore they rotate together. Withdrawal of the closure device 100 from the tissue puncture 118 (if the anchor 108 is deployed and the gearbox assembly 182 has contacted the stop 161) causes the suture 104 to unwind from the spool 184. The spool 184 rotates as the suture 104 unwinds and provides a torsional motive force that is transduced to a linear compacting force.

The torsional motive force provided by the spool 184 is transduced into the linear compacting force by the gearbox assembly 182. The gearbox assembly 182 includes the first gear 186 arranged coaxially with the spool 184. The first gear 186 may be arranged adjacent to a second gear 188. The second gear 188, when assembled, engages the first gear 186. The second gear 188 may be a two-stage gear, with each stage engaging a different adjacent gear as shown. The first and second gears 186, 188 may engage one another with a frictional fit, or with meshed gear teeth as shown. The second gear 188 is arranged adjacent to a third gear 190. When assembled, the second gear 188 engages and drives the third gear 190.

The compacting tube 112 is disposed between the third gear 190 and a guide 192. The compacting tube 112 preferably includes the teeth shown, which mesh with teeth of the third gear 190. A concave holder 196 may support the compacting tube 112. When the spool 184 rotates, it drives the compacting tube 112, which in turn compacts the sealing plug 110 (see FIG. 6). Alternatively, the compacting tube 112 may not extend into the housing 152, and instead a separate rack may mesh with the third gear 190. The separate rack would, in turn, drive the compacting tube 112.

The compacting tube 112 is preferably semi-tubular and partially disposed about the suture 104 along its longitudinal axis. The compacting tube structure permits the suture and the compacting tube to merge as the spool 184 unwinds. The suture 104 and the compacting tube 112 are not fixedly connected to one another, allowing each to slide freely past the other. Accordingly, with the anchor 108 deployed, as the closure device 100 is retracted in a first direction with the gearbox assembly 182 bearing against the stop 161 (see FIG. 6), the suture 104 unwinds from the spool 184, which drives the gearbox assembly 182. The gearbox assembly 182 drives the compacting tube 112 in a second, opposite direction, and the compacting tube compacts the sealing plug 110 (see FIG. 6).

As described above, the general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Referring now to FIGS. 9-14, a medical device, for example a tissue puncture closure device 200 (also referred to herein as a "vascular closure device" and a "closure device"), is shown according to one embodiment of the present disclosure. The closure device 200 is shown in an assembly view in FIG. 9 in combination with a procedure sheath 116. The closure device 200 and procedure sheath 116 are inserted through a percutaneous incision 219 and vessel puncture 218.

Referring now to FIGS. 9-14, a medical device, for example a tissue puncture closure device 200 (also referred to herein as a "vascular closure device" and a "closure device"), is shown according to one embodiment of the present disclosure. The closure device 200 is shown in an assembly view in FIG. 9 in combination with a procedure sheath 216. The closure device 200 and procedure sheath 116 are inserted through a percutaneous incision 219 and vessel puncture 218.

The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause nearly immediate hemostasis of the blood vessel (e.g., arterial or vascular) puncture. However, it will be understood that while the description of the embodiments below are directed to the sealing off of percutaneous punctures in vessels, such devices have much more wide-spread applications and can be used for sealing punctures or incisions in other types of tissue walls as well. Thus, the sealing of a percutaneous puncture in a vessel, shown herein, is merely illustrative of one particular use of the closure device 200 of the present disclosure.

The closure device 200 includes a first or proximal end portion 206 and a second or distal end portion 207. A carrier tube 202 extends from the proximal end portion 206 to the distal end portion 207 and includes an outlet 213 at the distal end portion 207. The distal end portion 207 may include a slit (not shown) that facilitates ejection of a sealing pad 210 from the carrier tube 202.

The carrier tube 202 may be made of plastic or other material and is designed for insertion through the procedure sheath 216. The procedure sheath 216 is designed for insertion through a percutaneous incision 219 and into the vessel 228. In at least one example, the vessel 228 is a femoral artery.

An anchor 208 and a sealing pad 210 may be positioned at the distal end portion 207 of the closure device 200. The anchor 208 of the present embodiment may be an elongated, relatively stiff, low-profile member arranged to be seated inside the vessel 228 against an internal vessel wall contiguous with the vessel puncture 218. The anchor 208 typically comprises a biologically resorbable polymer. The sealing pad 210 may be formed of, for example, a compressible sponge, foam, or fibrous mat made of a hemostatic biologically resorbable material such as collagen. The sealing pad 210 may be configured in any shape so as to facilitate sealing the vessel puncture 218. Some example shapes and sizes of particular relevance to the present disclosure are described in further detail below related to FIGS. 15-26.

The sealing pad 210 and anchor 208 are connected to one another by a suture 204. The suture 204 typically comprises a biologically resorbable material. The anchor 208, the sealing pad 210, and the suture 204 are collectively referred to as the "closure elements" below.

As shown in FIG. 9, and similar to the arrangement shown in FIG. 1, the anchor 208 is initially arranged adjacent to and exterior of the distal end portion 207 of the carrier tube 202, while the sealing pad 210 is initially disposed within the carrier tube 202. The anchor 208 is shown nested in its low profile configuration along the carrier tube 202 to facilitate insertion into the vessel 228.

The suture 204 extends distally from the first end portion 206 of the closure device 200 through the carrier tube 202. The suture 204 may be threaded through one or more perforations in the sealing pad 210, through a hole in the anchor 208, and proximally back toward the carrier tube 202 to the sealing pad 210. The suture 204 is preferably threaded again through a perforation or series of perforations in the sealing pad 210. The suture 204 may also be threaded around itself to form a self-tightening slip-knot. The suture 204 may thus connect the anchor 208 and the sealing pad 210 in a fixed arrangement relative to each other. Alternatively, the suture 204 may be connected to the anchor 208 in a pulley-like arrangement to cinch the anchor 208 and the sealing pad 210 together when the carrier tube 202 is pulled away from the anchor 208 and the sealing pad 210. The anchor 208 and the sealing pad 210 sandwich and lock the anchor and sealing plug together, sealing the vessel puncture 218.

The carrier tube 202 houses a positioning member 212 that is configured to maintain a position of the sealing pad 210 relative to the vessel puncture 218 while the carrier tube 202 and procedure sheath 216 are withdrawn from the percutaneous incision 219. The positioning member 212 is shown located within the carrier tube 202 and proximal of the anchor 208. The positioning member 212 also extends into a housing 224 of the closure device 200. The positioning member 212 is preferably an elongated tubular or semi-tubular member that may be rigid or flexible and formed of any suitable material. For example, according to one embodiment, the positioning member 212 comprises a polyurethane material. The suture 204 extends through at least a portion of the positioning member 212. For example, as shown in FIGS. 9-14, the suture 204 extends along the positioning member 212 between the proximal and distal end portions 206, 207. Typically, the suture 204 is not directly connected to the positioning member 212. Accordingly, the suture 204 and the positioning member 212 may slide past one another.

The suture 204 may extend proximally into the housing 224 and be collected onto a suture spool 236. The suture spool 236 may be carried on at least one slide member within the housing. In one arrangement, the closure device 200 includes a first slide 230 and a second slide 232. The suture spool 236 is carried by the second slide 232. The second slide 232 is carried by and is slideable relative to the first slide 230. The first slide 230 is slideably mounted in the housing 224 of the closure device 200. The housing 224 may include a first release surface 226 arranged to contact a portion of the first slide 230 as described in further detail below.

The first slide 230 includes a distal end 238, a first release member 240, and a second release surface 242. The first slide 230 is arranged within the housing 224 and is movable between at least the retracted or first position shown in FIG. 9 and the extended or second position shown in FIGS. 11 and 13. The first slide 230 maintains the retracted position during insertion of the closure device 200 into the procedure sheath 216 and insertion into the vessel 228 (see FIG. 9).

The first slide 230 is held in the retracted position with a release mechanism. The release mechanism may include, for example, the first release member 240 and the first release surface 226. Typically, the first release member 240 engages the first release surface 226 to hold the first slide 230 in the retracted position until at least one of the first release member 240 and first release surface 226 is activated. Activation of the first release member 240 to release from the first release surface 226 may occur automatically upon application of a predetermined amount of force applied in an axial direction (i.e., a direction along the length dimension of procedure sheath 216) to the first slide 230. The force in the axial direction may be applied by withdrawing the closure device 200 and procedure sheath 216 in the direction X while the anchor 208 is engaged with an inner surface of the vessel 228 as shown in FIG. 9. This predetermined amount of axially applied force provides disengagement of the first release member 240 from the first release surface 226.

The predetermined amount of force applied in the axial direction to the first slide 230 to provide automatic movement of the first slide 230 relative to the housing 224 is typically in the range of about 0.3 lbs to about 2.0 lbs., and more preferably in the range of about 0.3 lbs. to about 1.0 lbs. Typically, the predetermined amount of force applied in the axial direction to the first slide 230 is no greater than about 1.0 lbs.

Figures 11, 12:
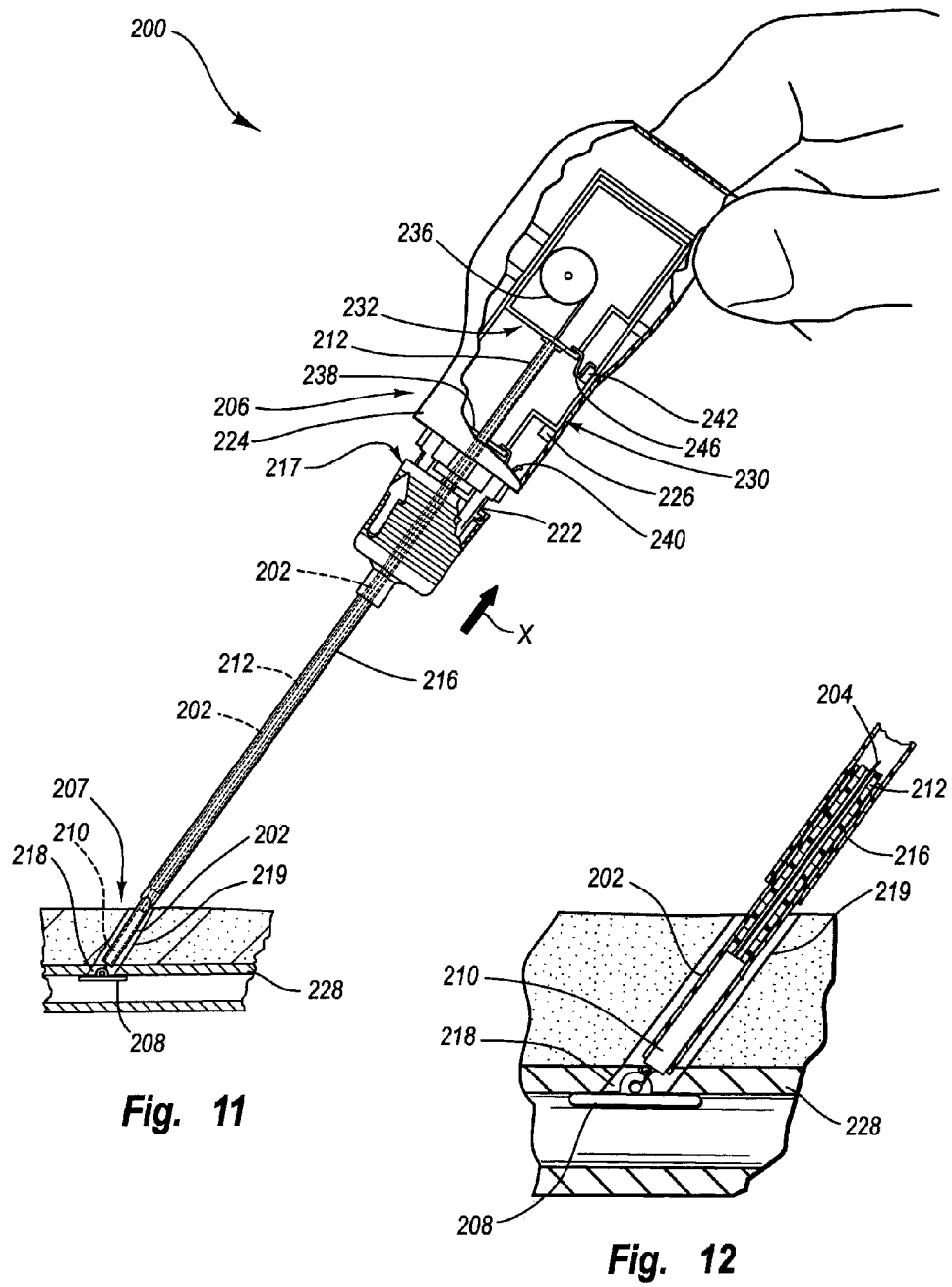
FIG. 11 is a side view of the tissue puncture closure device of FIG. 9 shown engaged with a vessel in a second position with the procedure sheath retracted.
FIG. 12 is a detailed inset of FIG. 11.
Figures 13, 14:
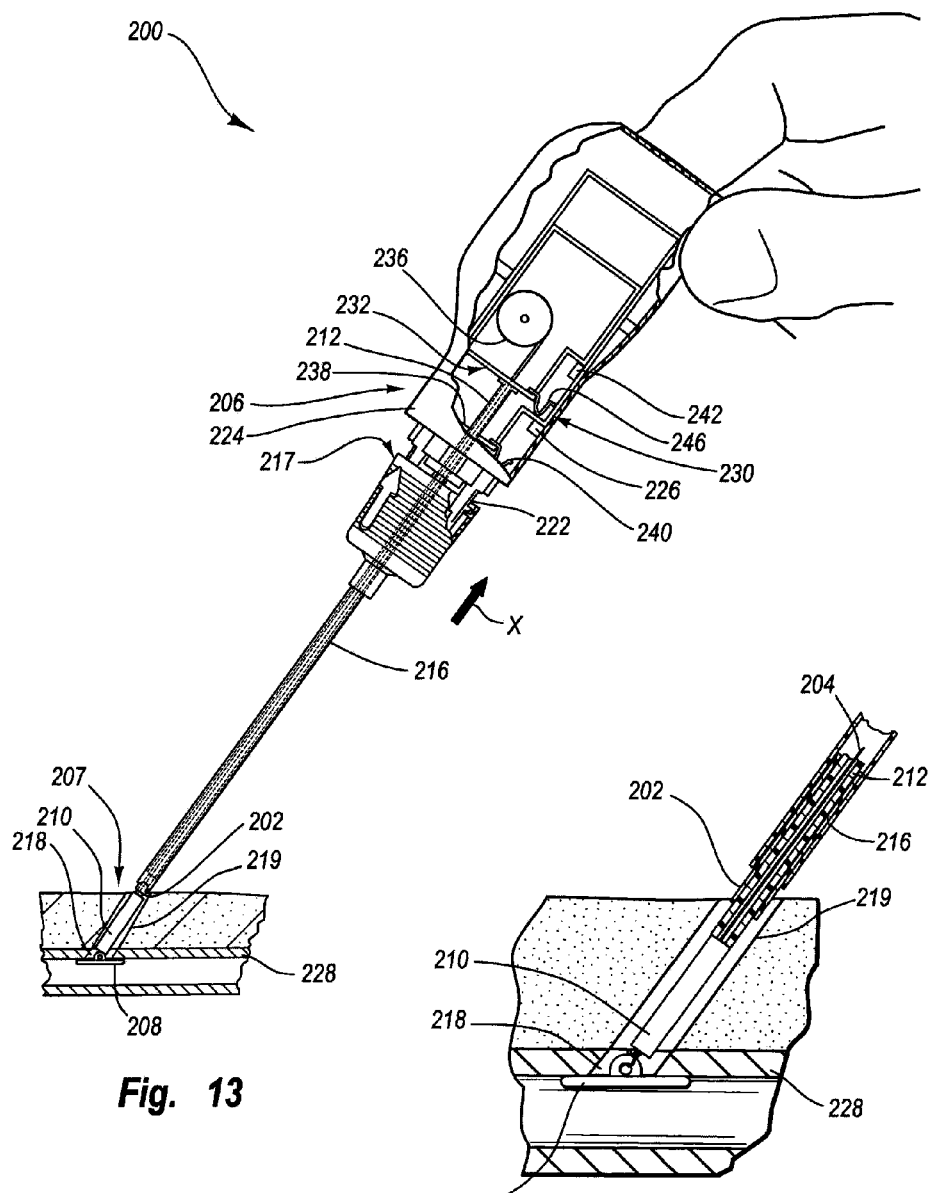
FIG. 13 is a side view of the tissue closure device of FIG. 9 shown engaged with a vessel in a third position with the carrier tube retracted.
FIG. 14 is a detailed inset of FIG. 13.

By permitting the first slide 230 to move from the retracted position shown in FIG. 9 to the advanced position shown in FIG. 11, the carrier tube 202 (which is connected to the first slide 230) and positioning member 212 (which is connected to the second slide 232) are able to maintain substantially the same position relative to the vessel puncture 218 while the housing 224 and procedure sheath 216 move proximally in the direction X relative to the vessel puncture 218. In at least one example, the procedure sheath 216 is removed from the vessel puncture 218 and percutaneous incision 219, and the carrier tube 202 remains in the percutaneous incision 219 when the first slide 230 moves from the retracted position shown in FIG. 9 to the advanced position shown in FIG. 11.

The second slide 232 includes a distal end 244 and a second release member 246. The second slide 232 is arranged within the housing 224 and is movable between at least the retracted or first position shown in FIG. 9 and the extended or second position shown in FIG. 11. The second slide 232 maintains the retracted position during insertion of the closure device 200 into the procedure sheath 216 and into the vessel 228 (see FIG. 9), retraction of the housing 224 and procedure sheath 216 in the direction X to the position shown in FIG. 11, and movement of the first slide into the advanced position shown in FIG. 11.

The second slide 232 may be held in the retracted position with a release mechanism. The release mechanism may include, for example, the second release member 246 and the second release surface 242. Typically, the second release member 246 engages the second release surface 242 of the first slide 230 to hold the second slide 232 in the retracted position until at least one of the second release member 246 and second release surface 242 is activated to disengage the second release member 246 from the second release surface 242. Activation of the second release member 246 and second release surface 242 may occur automatically upon application of a predetermined amount of force applied in the axial direction (i.e., a direction along the length dimension of procedure sheath 216) to the second slide 232. This force in the axial direction can be applied by withdrawing the closure device 200 and procedure sheath 216 in the direction X while the anchor 208 is engaged with an inner surface of the vessel 228 and the first slide 230 is positioned in the advanced position shown in FIG. 13. This predetermined axially applied force provides disengagement of the second release member 246 from the second release surface 242.

The predetermined amount of force applied in the axial direction to the second slide 232 to provide automatic movement of the second slide 232 relative to the first slide 230 is typically in the range of about 0.3 lbs to about 2.0 lbs., and more preferably in the range of about 0.3 lbs. to about 1.0 lbs. Typically, the predetermined amount of force applied in the axial direction to the second slide 232 is no greater than about 1.0 lbs.

The carrier tube 202 is typically connected to the first slide 230 and the positioning member 212 is typically connected to the housing 224. By permitting the second slide 232 to move from the retracted position shown in FIGS. 9 and 11 to the advanced position shown in FIG. 13, the sealing pad 210 and positioning member 212 are able to maintain substantially the same position relative to the vessel puncture 218 while the housing 224, procedure sheath 216, and carrier tube 202 move proximally in the direction X relative to the vessel puncture 218. In at least one example, the carrier tube 202 is removed from the vessel puncture 218 and percutaneous incision 219 when the second slide 232 moves from the retracted position shown in FIG. 11 to the advanced position shown in FIG. 13.

The first and second slides 230, 232 may be configured to automatically release to move relative to the housing 224 and to each other upon application of a predetermined amount of force applied in the axial direction, as described above. The predetermined amount of force for release of each of the first and second slides 230, 232 may be different. For example, the predetermined amount of force may be least for release of the first slide 230, and a greater amount for the second slide 232. In some arrangements, the second slide 232 is not able to release until after the first slide 230 has been released.

In other arrangements, at least one of the first and second slides 230, 232 are released manually to move relative to the housing 224 or to each other by the operator of closure device 200. In some arrangements, the closure device 200 includes visual or audible features that indicate to the operator when features of the closure device 200 have attained certain positions. For example, the closure device 200 may include a window into the housing 224 and at least one position marker so the operator can see when the first slide 230 has reached the advanced position shown in FIG. 11, which indicates to the operator that the second slide can be released manually.

In other arrangements, second slide 232 is eliminated from the closure device. The suture spool 236 may be mounted directly to the first slide 230. Portions of the positioning member 212 may be collected on and carried by the first slide 230. In one example, a portion of the positioning member 212 is collected on a spool member that is carried by the first slide 230. The spool upon which the positioning member 212 is carried (a positioning member spool) may be co-axial with the suture spool 236. In some arrangements, the suture spool 236 and positioning member spool may be connected together to rotate together. A closure device that includes example suture spools and a positioning member is disclosed in U.S. Published Application No. 2005/0125031, which is hereby incorporated in its entirety by this reference.

In still further arrangements, it may be possible to construct the closure device without the first and second slides 230, 232. Various gears, spools, and other mechanisms may be used to permit release of portions of the carrier tube 202, suture 204, and positioning member 212 relative to the housing 224 and procedure sheath 216 to deploy and maintain a position of the sealing pad 210 within the percutaneous incision 219.

In practice, the carrier tube 202 (containing the closure elements described above) is inserted into the procedure sheath 216, which is already inserted within the vessel 228. As the closure device 200 and the associated closure elements are inserted into the procedure sheath 216, the anchor 208 passes through and out of the distal end of the procedure sheath 216 and is inserted into the vessel 228. The anchor 208 may initially be arranged substantially flush with the carrier tube 202 to facilitate insertion of the anchor 208 through the percutaneous incision 219 and into the vessel 228.

After the anchor 208 passes out of the distal end of the procedure sheath 216, the anchor 208 tends to deploy or rotate to the position shown in FIGS. 9-10. The closure device 200 may be partially withdrawn, catching the anchor 208 on the distal end of the procedure sheath 216 and rotating the anchor 208 to the position shown in FIGS. 9-10. The closure device 200 typically includes a pair of sheath connection members 222 that are lockingly received by a matching pair of recesses (not shown) in a proximal surface of the hub portion 217 of the procedure sheath 216. The locking arrangement between the sheath connection members 222 and matching recesses in the procedure sheath 216 limits movement between the housing 224 and the procedure sheath 216.

Following deployment of the anchor 208, the housing 224 and the procedure sheath 216 are withdrawn together. Withdrawing the housing 224 a first retraction distance causes the anchor 208 to anchor itself against an internal wall of the vessel 228. With the anchor 208 anchored within the vessel 228, retracting the housing 224 and procedure sheath 216 in the direction X a second retraction distance releases the first slide 230 to permit relative movement between the housing 224 and the first slide 230 that results in the procedure sheath 216 retracting out of the puncture tract 119 (see FIGS. 11-14). The housing 224 and procedure sheath 216 are retracted the second retraction amount in the direction X until the first slide 230 reaches the advanced position in the housing 224 shown in FIG. 9.

Retracting the housing 224 and procedure sheath 216 a third retraction distance after completion of retracting the second retraction distance exposes the sealing pad 210 out from the distal end portion 207 of the carrier tube 202, thereby depositing the sealing pad 210 within the percutaneous incision 219. The slit (not shown) in the carrier tube 202 may provide improved ease in ejecting the sealing pad 210.

As described above, the carrier tube 202 is connected to the first slide 230 and the positioning member 212 is connected to the second slide 232. Applying a retraction force in the direction X after retracting the second retraction distance releases the second slide 232 to move axially relative to the first slide 230 so that the positioning member 212 maintains the same position relative to the percutaneous incision 219 and the carrier tube 202 retracts out of the percutaneous incision 219 to expose the sealing pad 210 (see FIG. 13). Retracting the housing 224 and procedure sheath 216 the third retraction distance moves the second slide 232 from the position shown in FIG. 11 to the advanced position shown in FIG. 13.

Applying a retraction force to the housing 224 in the direction X after the housing 224, procedure sheath 216, and carrier tube 202 have been retracted the second retraction distance may cause a portion of the suture 204 to unwind from the suture spool 236. In at least some arrangements, the suture spool 236 is released for rotation by manually activating a spool release mechanism (not shown in the figures). The spool release mechanism may be accessible from outside of the housing 224 for contact by the operator. Unwinding the suture spool 236 exposes a sufficient length of the suture 204 to allow an operator to easily cut the suture 204 and separate the sealing pad 210 and anchor 208 from the remainder of the closure device 200.

In some arrangements, the suture spool 236 may be rotatable in a first rotation direction to apply tension to the suture 204 to pull the suture 204 in a direction away from the anchor 208 and sealing pad 210 as the housing 224 is retracted in the direction X through the first and second retraction distances.

The tension in the suture applied by the suture spool 236 may help cinch and lock (with a slip knot or the like) together the anchor 208 and the sealing pad 210, sandwiching a wall of the vessel 228 between the anchor 208 and sealing pad 210. An axial force exerted by the cinching together of the anchor 208 and sealing pad 210 by the suture 204 may be sufficient to hold the anchor 208 and sealing pad 210 together and in contact with the vessel 228 adjacent to the vessel puncture 218. This cinching force may be applied without changing a shape of the sealing pad 210. In at least some arrangements, neither this cinching force nor the deployment of the sealing pad from the closure device 200 into the percutaneous incision 219 adjacent to the vessel puncture 218 results in deformation of the sealing pad. Any forces applied to the sealing pad 210 during cinching and deploying of the sealing pad may temporarily change the size of a portion of the sealing pad (i.e., a length or cross-sectional size) without changing a shape (i.e., cross-sectional shape) of the sealing pad 210.

In other arrangements, a size or shape of the sealing pad 210 may be altered when moving the sealing pad 210 from within the carrier tube (i.e., the sealing pad may be compressed to fit into the carrier tube) to when the sealing pad 210 is being exposed and deployed within the percutaneous incision. In some arrangements, the sealing pad 210 may not change in size or shape between when being exposed and deployed in the percutaneous incision and after completion of cinching the sealing pad and anchor together. In still further arrangements, a size or shape of the sealing pad 210 is constant from when the sealing pad 210 is positioned in the carrier tube to when the sealing pad 210 is exposed and deployed within the percutaneous incision, but before being cinched together with the anchor.

Figure 15:
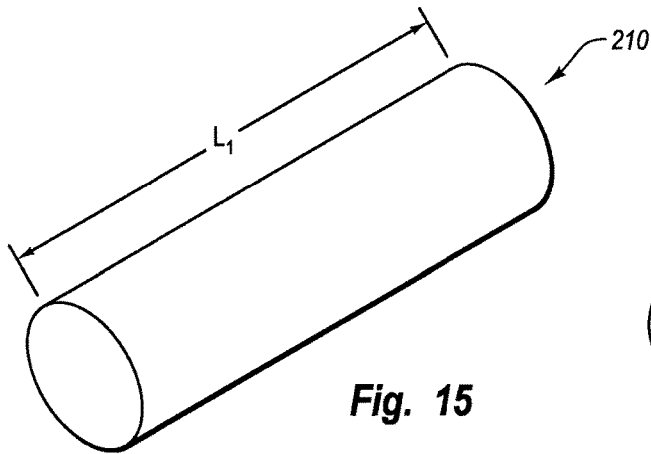
FIG. 15 is a perspective view of an example sealing pad according to the present disclosure for use with the tissue closure device of FIG. 9.
Figure 16:
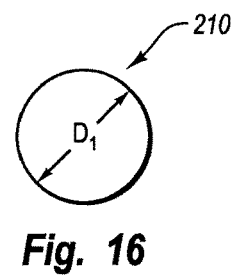
FIG. 16 is an end view of the sealing pad of FIG. 15 in an unexpanded state.
Figure 17:
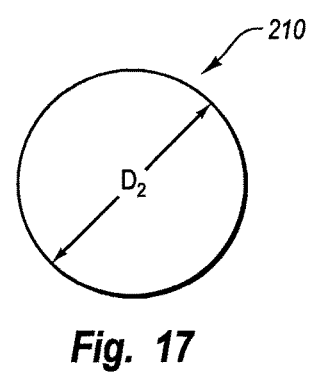
FIG. 17 is an end view of the sealing pad of FIG. 15 in an expanded state.

The sealing pad 210 shown in FIGS. 9-14 has a generally elongate, cylindrical structure. FIGS. 15-17 illustrate the sealing pad 210 in greater detail. FIGS. 15 and 16 show the sealing pad 210 in an unexpanded state having a length $L_1$ and a diameter $D_1$ prior to absorbing a liquid. As discussed above, the size (i.e., length $L_1$ and diameter $D_1$) and shape may vary prior to absorbing a liquid, such as prior to and after deployment from the carrier tube 202 or prior to and after cinching to the anchor 208 with the suture 204. In other arrangements, the size (i.e., length $L_1$ and diameter $D_1$) and shape may remain constant or substantially constant prior to absorbing a liquid, such as prior to and after deployment from the carrier tube 202 or prior to and after cinching to the anchor 208 with the suture 204.

A size of the sealing pad 210 may increase upon absorption of a liquid such as blood. In one example, the diameter or maximum outer dimension of the sealing pad 210 may change from $D_1$ to $D_2$ upon absorption of a liquid, wherein $D_2$ is greater than $D_1$ (see FIGS. 16 and 17). In some arrangements, the length $L_1$ of the sealing pad 210 may also change (i.e., increase or decrease) upon absorption of a liquid.

Figure 18:
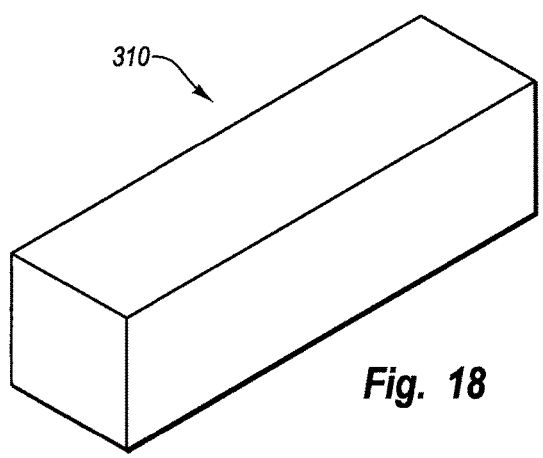
FIG. 18 is a perspective view of another example sealing pad according to the present disclosure for use with the tissue closure device of FIG. 9.
Figure 19:
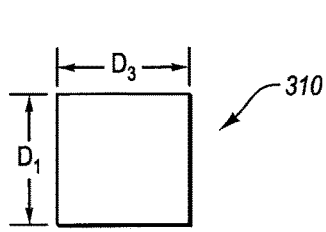
FIG. 19 is an end view of the sealing pad of FIG. 18 in an unexpanded state.
Figure 20:
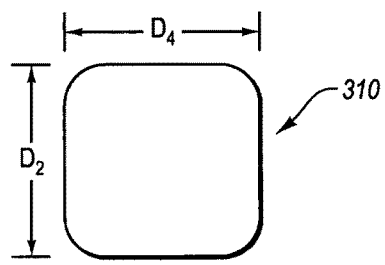
FIG. 20 is an end view of the sealing pad of FIG. 18 in an expanded state.

Other constructions are possible for the sealing pad used with the closure devices disclosed herein. Referring to FIGS. 18-20, a sealing pad 310 having a non-circular cross-sectional shape is shown. The sealing pad 310 has a generally square cross-sectional shape with dimensions $D_1$ and $D_3$ between opposing sides. The shape and size of the sealing pad 310 may change upon absorption of a liquid. For example, the sealing pad 310 may expand to greater dimensions $D_2$ and $D_4$ between opposing sides upon absorption of a liquid. The shape of the sealing pad 310 may change from the rectangular shaped cross-section of FIG. 19 with pointed corners, to the rectangular shaped cross-section of FIG. 20 having rounded corners or other alterations from the shape of FIG. 19.

In some arrangements, the dimensions $D_1$ and $D_3$ are substantially the same to provide a square shaped cross-section. In other examples, the dimension $D_1$ is greater than the dimension $D_3$ to provide a rectangular shape with unequal side lengths. Typically, the dimension $D_1$ is no greater than about 4 times the dimension $D_3$, and more preferably is not greater than about 2 times the dimension $D_3$.

FIGS. 21-23 illustrate further example cross-sectional shapes possible for a sealing pad in accordance with the present disclosure. FIG. 21 shows a sealing pad 410 having a generally triangular cross-sectional shape. FIG. 22 shows a sealing pad 510 having a generally hexagonal cross-sectional shape. FIG. 23 shows a sealing pad 610 having a generally oval cross-sectional shape. Many other cross-sectional shapes, including, for example, X-shape, V-shape, and C-shape cross-sectional shapes are possible including variations of the cross-sectional shapes shown in FIGS. 15-23. Further, the sealing pads may be folded or secured to other sealing pad portions to create any desired cross-sectional shape.

The cross-sectional shape of the sealing pads disclosed herein may be relatively constant along the length (i.e., length $L_1$) of the sealing pad. In other arrangements, the cross-sectional shape may vary along the length. For example, the cross-sectional shape may be generally circular at one end of the sealing pad and may transition to a different cross-sectional shape (e.g., oval or square) at an opposite end of the sealing pad.

The minimum thickness dimension of the sealing pads described herein (i.e., $D_1$ and $D_3$) prior to absorption of a liquid is typically no less than about 0.5 mm to about 1.0 mm, and no more than about 2.0 mm to about 2.5 mm.

The sealing pad 210 discussed above may be connected to the anchor 208 with various suture arrangements. Different suture arrangements may influence how well a position of the sealing pad 210 is maintained relative to the tissue puncture and to the anchor 208. The suture arrangement may also influence whether a shape or size of the sealing pad 210 is changed when the suture 204 is used to cinch the sealing pad 210 and anchor 208 together. A position of a suture knot 297 and a position of longitudinal and lateral apertures 298, 299 through which the suture 204 passes may also be relevant.

FIGS. 24A-B, 25A-B and 26A-B illustrate several example suture arrangements that provide a connection between the anchor 208 and the sealing pad 210. FIGS. 24A, 25A and 26A illustrate the suture 204 with a loose fit about the sealing pad 210 to more clearly illustrate a path for the suture 204 relative to the anchor 208 and sealing pad 210. FIGS. 24B, 25B and 26B illustrate the suture 204 in a close or tight fit about the sealing pad 210 with the anchor 208 drawn into contact with the sealing pad 210.

Referring to FIGS. 24A-B, the sealing pad 210 includes a longitudinal aperture 298 that extends between opposing end surfaces of the sealing pad. A first portion 204A of the suture extends through the longitudinal aperture 298 to the anchor 208. A second portion 204B of the suture extends from the anchor 208 proximally to a position proximal of the sealing pad 210 where a suture knot 297 is formed between the first and second portions 204A, 204B. The suture knot 297 may be contacted against a proximal end of the sealing pad as a tension force is applied in the suture 204 in the proximal direction thereby cinching the sealing pad 210 toward the anchor 208.

Referring to FIGS. 25A-B, the sealing pad 210 includes a lateral aperture 299 that extends laterally through the sealing pad 210 between opposing sides. A first portion 204A of the suture extends adjacent to the sealing pad 210 between opposing ends of the sealing pad to contact with the anchor 208. The second portion 204B extends from the anchor 208 and through the lateral aperture 299 where a suture knot 297 is formed between the first and second portions 204A, 204B. The lateral aperture 299 may be oriented perpendicular to a longitudinal dimension of the sealing pad 210. The lateral aperture 299 may be positioned closer to one end of the sealing pad 210 than other, such as closer to the distal end (see FIGS. 25A-B). Alternatively, the lateral aperture 299 may extend at a non-perpendicular angle through the sealing pad 210 relative to the longitudinal dimension. The suture knot 297 may be contacted against a proximal end of the sealing pad as a tension force is applied in the suture 204 in the proximal direction thereby cinching the sealing pad 210 toward the anchor 208.

FIGS. 26A-B illustrate the sealing pad 210 including a longitudinal aperture 298 that extends between opposing end surfaces of the sealing pad, and a lateral aperture 299 that extends laterally through the sealing pad. The longitudinal aperture 298 may intersect the lateral aperture 299 to define a continuous pathway for the suture 204 to pass through. A first portion 204A of the suture extends from a proximal end of the sealing pad 210 along an exterior thereof, through a first opening of the lateral aperture 299, and through a distal portion of the longitudinal aperture 298 to the anchor 208. A second portion 204B of the suture extends from a proximal end of the sealing pad 210 along an exterior thereof, through a second opening of the lateral aperture 299, and through the distal portion of the longitudinal aperture 298 to the anchor 208. The first and second suture portions 204A, 204B may intersect at a location proximal of a proximal end of the sealing pad 210 where a suture knot 297 is formed.

The lateral aperture 299 may be oriented perpendicular to a longitudinal dimension of the sealing pad 210 as shown in FIGS. 26A-B. The lateral aperture 299 may be positioned closer to one end of the sealing pad 210 than other. Alternatively, the lateral aperture 299 may extend at a non-perpendicular angle through the sealing pad 210 relative to the longitudinal dimension. The suture knot 297 may contact or bear against a proximal end of the sealing pad as a tension force is applied in the suture 204 in the proximal direction thereby cinching the sealing pad 210 toward the anchor 208.

In other arrangements, the suture portions 204A, 204B may extend through a proximal portion of a longitudinal aperture 298 that is positioned proximal of the lateral aperture 299, extend through the lateral aperture 299, and then extend distally to the anchor 208. In further arrangements, both of the suture portions 204A, 204B may extend through the same portion of the lateral aperture 299 to the longitudinal aperture 298 as compared to extending through different portions as shown in FIGS. 26A-B.

The suture 204 is used primarily to retain the anchor 208 and sealing pad 210 together. The suture 204, including cinched suture knot 297, may provide a minimum amount of force to retain the anchor 208 and sealing pad 210 against opposing inner and outer surfaces of the tissue puncture (i.e., vessel puncture 218). Although it may be possible to provide sufficient tension in the suture 104 to cause some deformation or compaction of the sealing pad 210, such levels of force are deemed required in order to provide retention between the anchor 208 and sealing pad 210.

Many other suture path arrangements may be possible. A shape or size of the sealing pad may influence the suture path options that are available. The suture path through the sealing pad is less significant as such suture paths are not required to provide certain deformation or compaction of the sealing pad. Some example alternative suture path arrangements for use with the sealing pads disclosed herein are described in U.S. Published Patent Application No. 2005/0125031, which application is hereby incorporated in its entirety by this reference.

The sealing pads disclosed herein may comprise, for example, a compressible sponge, foam, or fibrous mat made of a hemostatic biologically resorbable material such as collagen. In some examples, the sealing pad comprises a substantially uncross-linked chemical structure, a substantially cross-linked chemical structure, or some other proportion of cross-linked or uncross-linked chemical structure. Cross-linked collagen materials may be effective at maintaining a substantially constant shape prior to and after deployment from a carrier tube of a closure device and before absorption of a fluid. A cross-linked collagen material may be configured to maintain a position within a percutaneous incision (e.g., percutaneous incision 219) adjacent to a tissue puncture (e.g., vessel puncture 218) after absorption of a fluid.

The sealing pads disclosed herein may comprises a single material. The sealing pad may be formed as a single, integral piece. Alternatively, the sealing pad may comprise at least two different materials. The sealing pad made be formed by securing together at least two pieces that were formed separately. In some arrangements, a sealing pad having multiple materials or multiple pieces may be formed together as a single piece using, for example, a co-molding process. In some example, apertures and other features may be formed in the sealing pad concurrent with formation of the sealing pad, such as in a molding process. Alternatively, apertures and other features may be formed in a post processing step such as drilling, stamping, or cutting.

The sealing pads disclosed herein may have a generally smooth surface along an exterior of the sealing pad. In one example, a side surface of the sealing pad that extends between opposing distal and proximal ends of the sealing pad comprises a substantially smooth surface without recess or protrusions. In other examples, a least one exterior surface of the sealing pad comprises a texture such as a plurality of grooves or bumps.

The sealing pads disclosed herein may be used with any closure device. In some arrangements, the sealing pads disclosed herein may be used with a closure device such as the closure device 100 that provides at least some compaction of the sealing pad. In at least some arrangements, there may be advantages related to the sealing pad construction or the suture arrangement for attachment of the sealing pad to the anchor from which a compaction closure device can benefit.

The preceding description has been presented only to illustrate and describe exemplary embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device for partial insertion into and sealing of a tissue wall puncture, comprising: a carrier tube, the carrier tube having a distal end, the distal end comprising a slit allowing the distal end of the carrier tube to flex or open; a suture extending from a first end of the closure device to a second end of the closure device; an anchor for insertion through the tissue wall puncture and being attached to the suture at the second end of the closure device; a sealing pad slidingly attached to the suture and carried in the carrier tube in a pre-deployment position, the sealing pad being longitudinally separated from the anchor, a first portion of the suture extending along a lateral exterior side of the sealing pad, a second portion of the suture passing through an aperture in the sealing pad in a direction parallel to a longitudinal direction of the sealing pad, and a suture knot being disposed between the first portion of the suture and the second portion of the suture, the sealing pad maintaining a constant shape and cross-sectional area from when positioned in the carrier tube to when removed from the carrier tube and configured to be positioned within a percutaneous incision leading to the tissue wall puncture in a post-deployment position.

2. A tissue puncture closure device according to claim 1, wherein the sealing pad includes a generally circular cross-sectional shape.

3. A tissue puncture closure device according to claim 1, wherein the sealing pad includes a non-circular cross-sectional shape.

4. A tissue puncture closure device according to claim 1, wherein the sealing pad is expandable in the post-deployment position upon absorption of a liquid.

5. A tissue puncture closure device according to claim 1, wherein the sealing pad is constructed as an integral, single piece member.

6. A tissue puncture closure device according to claim 1, further comprising a housing positioned at the first end of the closure device, and at least one slide member positioned in and movable relative to the housing.

7. A tissue puncture closure device according to claim 6, wherein the at least one slide member includes first and second slides, the second slide being positioned in and movable relative to the housing, and the first slide being carried by and movable relative to the second slide.

8. A tissue puncture closure device according to claim 7, further comprising a positioning member positioned in the carrier tube and in contact with a proximal end of the sealing pad, the positioning member being connected to the second slide, and the suture extending through an interior of the positioning member.

9. A tissue puncture closure device according to claim 8, wherein the positioning member maintains a position adjacent to the sealing pad while the carrier tube is withdrawn proximally relative to the sealing pad to provide the sealing pad in the post-deployment position, and the positioning member is removed from contact with the sealing pad without changing a shape or size of the sealing pad.

10. A tissue puncture closure device according to claim 6, further comprising a suture spool having a portion of the suture wound thereon, the suture spool being carried by the at least one slide member.

11. A tissue puncture closure device according to claim 6, further comprising an insertion sheath through which the carrier tube is inserted, the insertion sheath being connected to the housing, and the carrier tube being connected to the at least one slide member.

12. A tissue puncture closure device according to claim 6, further comprising at least one automatic release member operable to release the at least one slide member to move upon withdrawal of the closure device from the tissue wall puncture.

13. The tissue puncture closure device according to claim 1, wherein the aperture is a longitudinal aperture in the sealing pad.

14. The tissue puncture closure device according to claim 13, further comprising a lateral aperture in the sealing pad, the longitudinal aperture intersecting the lateral aperture such that the suture extends continuously through the longitudinal aperture and the lateral aperture.

15. A tissue puncture closure device for partial insertion into and sealing of a tissue puncture in an internal tissue wall, comprising: an anchor configured for positioning on a distal side of the internal tissue wall; a sealing pad configured for deployment from the tissue puncture closure device within a percutaneous incision on a proximal side of the internal tissue wall;
    a suture connected at a distal end to the anchor and sealing pad for slideably cinching the anchor and sealing pad together about the tissue puncture, the anchor and the sealing pad each being separately connected to the suture, the sealing pad being slideably disposed on the suture proximal of the anchor, a first portion of the suture extending along a lateral exterior side of the sealing pad and a second portion of the suture passing through a longitudinal aperture in the sealing pad, the second portion extending parallel to a longitudinal direction of the sealing pad, and a suture knot being disposed between the first portion of the suture and the second portion of the suture, the sealing pad maintaining a constant shape and cross-sectional area prior to and after being cinched to the anchor with the suture.

16. The tissue puncture closure device according to claim 15, further comprising a positioning member disposed on the suture and positioned proximal of the sealing pad, the positioning member maintaining the sealing pad in a fixed position relative to the tissue puncture prior to and after deployment of the sealing pad on the proximal side of the internal tissue wall.

17. The tissue puncture closure device according to claim 15, further comprising:
    a housing arranged proximal of the anchor and sealing pad;
    a storage spool positioned in the housing onto which a proximal end of the suture is wound.

18. The tissue puncture closure device according to claim 17, further comprising a carrier tube, the sealing pad being positioned in the carrier tube prior to deployment, and a proximal end of the carrier tube terminating in the housing.

19. The tissue puncture closure device according to claim 18, further comprising a first slide member positioned in and movable relative to the housing, the carrier tube being connected to the first slide member, the first slide member carrying the storage spool.

20. A method of sealing a puncture in a vessel, the puncture being accessible through a percutaneous incision, the method comprising: providing a tissue puncture closure device including a suture, an anchor, and a sealing pad, the sealing pad being longitudinally separated from the anchor, a first portion of the suture extending along a lateral exterior side of the sealing pad and a second portion of the suture passing through a longitudinal aperture of the sealing pad, the second portion extending parallel to a longitudinal direction of the sealing pad, and a suture knot being disposed between the first portion of the suture and the second portion of the suture; inserting the anchor through the puncture and into the vessel; positioning the sealing pad within the percutaneous incision in a pre-deployment position; deploying the sealing pad from the tissue puncture closure device within the percutaneous incision and outside of the vessel; wherein the sealing pad maintains a constant shape and cross-sectional area from the pre-deployment position to a post-deployment position.

21. The method of claim 20, further comprising providing an insertion sheath, and the tissue puncture closure device further includes a carrier tube, the sealing pad being positioned in the carrier tube in the pre-deployment position, the method further comprising inserting the insertion sheath into the puncture, and inserting the anchor includes inserting the anchor through the insertion sheath and into the vessel.

22. The method of claim 20, further comprising cinching the sealing pad and anchor together with the suture, wherein the sealing pad maintains a constant shape prior to and after being cinched.

23. The method of claim 21, further comprising a positioning member positioned in the carrier tube proximal of the sealing pad, wherein deploying the sealing pad in the percutaneous incision includes withdrawing the carrier tube and maintaining the sealing pad in a fixed position relative to the puncture with the positioning member without compacting the sealing pad.

* * * * *